US011937995B2

(12) United States Patent
Sorimoto et al.

(10) Patent No.: US 11,937,995 B2
(45) Date of Patent: Mar. 26, 2024

(54) CAP, IMAGE CAPTURING DEVICE, DATA GENERATION SYSTEM, AND DATA GENERATION METHOD

(71) Applicant: J. MORITA MFG. CORP., Kyoto (JP)

(72) Inventors: Keisuke Sorimoto, Kyoto (JP); Mikinori Nishimura, Kyoto (JP)

(73) Assignee: J. MORITA MFG. CORP., Kyoto (JP)

( * ) Notice: Subject to any disclaimer, the term of this patent is extended or adjusted under 35 U.S.C. 154(b) by 347 days.

(21) Appl. No.: 17/149,641

(22) Filed: Jan. 14, 2021

(65) Prior Publication Data
US 2021/0212806 A1 Jul. 15, 2021

(30) Foreign Application Priority Data
Jan. 15, 2020 (JP) ................. 2020-004242

(51) Int. Cl.
*A61B 1/24* (2006.01)
*A61B 1/00* (2006.01)
*A61B 5/05* (2021.01)
*A61B 5/107* (2006.01)
(Continued)

(52) U.S. Cl.
CPC ........ *A61C 9/0053* (2013.01); *A61B 1/00006* (2013.01); *A61B 1/00009* (2013.01); *A61B 1/00137* (2013.01); *A61B 1/00172* (2013.01); *A61B 1/00193* (2013.01); *A61B 1/24* (2013.01); *A61B 5/1076* (2013.01); *A61B 5/1079* (2013.01); *A61C 9/006* (2013.01); *A61C 9/0066* (2013.01); *A61C 13/0003* (2013.01)

(58) Field of Classification Search
None
See application file for complete search history.

(56) References Cited

U.S. PATENT DOCUMENTS

| 9,039,418 B1 | 5/2015 | Rubbert |
| 2010/0189341 A1 | 7/2010 | Oota et al. |
| 2010/0268069 A1 | 10/2010 | Liang |

(Continued)

FOREIGN PATENT DOCUMENTS

| CN | 101822526 A | 9/2010 |
| CN | 101862182 A | 10/2010 |

(Continued)

OTHER PUBLICATIONS

Combined Chinese Office Action and Search Report dated Oct. 17, 2022, in corresponding Chinese Patent Application No. 2021100492519 (with English Translation and English Translation of Category of Cited Documents), 7 pages.

(Continued)

*Primary Examiner* — Samuel D Fereja
(74) *Attorney, Agent, or Firm* — Oblon, McClelland, Maier & Neustadt, L.L.P.

(57) ABSTRACT

A cap mountable on and detachable from an intraoral scanner including a housing having an opening for connecting to at least a part of the intraoral scanner, a measurement window provided in the housing and located opposite to the opening, and a mirror that reflects light from the measurement window toward the opening. The housing has a longitudinal length shorter than that of a probe defining a depth-of-field, of the intraoral scanner extending from the measurement window to a predetermined extent.

6 Claims, 12 Drawing Sheets

(51) Int. Cl.
*A61C 9/00* (2006.01)
*A61C 13/00* (2006.01)

(56) References Cited

U.S. PATENT DOCUMENTS

| | | | |
|---|---|---|---|
| 2012/0092461 | A1 | 4/2012 | Fisker et al. |
| 2014/0146142 | A1 | 5/2014 | Duret et al. |
| 2015/0018613 | A1 | 1/2015 | Hollenbeck et al. |
| 2015/0054922 | A1 | 2/2015 | Fisker et al. |
| 2015/0079535 | A1 | 3/2015 | Hollenbeck et al. |
| 2016/0220105 | A1 | 8/2016 | Duret |
| 2016/0256054 | A1 | 9/2016 | Hollenbeck et al. |
| 2017/0319308 | A1 | 11/2017 | Moon et al. |
| 2018/0098691 | A1 | 4/2018 | Wang et al. |
| 2018/0255923 | A1 | 9/2018 | Fisker et al. |
| 2019/0117078 | A1* | 4/2019 | Sharma .................. A61B 1/24 |
| 2019/0124323 | A1 | 4/2019 | Fisker et al. |
| 2019/0200006 | A1 | 6/2019 | Fisker et al. |
| 2019/0247163 | A1 | 8/2019 | Wu et al. |
| 2019/0289283 | A1 | 9/2019 | Fisker et al. |
| 2019/0293414 | A1 | 9/2019 | Sorimoto |
| 2020/0169722 | A1 | 5/2020 | Fisker et al. |
| 2022/0061786 | A1* | 3/2022 | Park .................. G01B 11/2518 |
| 2022/0167839 | A1* | 6/2022 | Do .......................... A61B 1/05 |

FOREIGN PATENT DOCUMENTS

| | | | |
|---|---|---|---|
| CN | 101940503 | A | 1/2011 |
| CN | 102429740 | A | 5/2012 |
| CN | 202235747 | U | 5/2012 |
| CN | 103025238 | A | 4/2013 |
| CN | 103782321 | A | 5/2014 |
| CN | 104349710 | A | 2/2015 |
| CN | 106491082 | A | 3/2017 |
| CN | 107106271 | A | 8/2017 |
| CN | 107529968 | A | 1/2018 |
| CN | 109124576 | A | 1/2019 |
| CN | 109475394 | A | 3/2019 |
| DE | 196 36 354 | A1 | 3/1998 |
| JP | 2011-24797 | A | 2/2011 |
| JP | 2014-61089 | A | 4/2014 |
| JP | 5654583 | | 11/2014 |
| JP | 2017-113389 | A | 6/2017 |
| JP | 2019-76461 | A | 5/2019 |
| WO | WO 2007/062658 | A2 | 6/2007 |
| WO | WO 2011/160102 | A2 | 12/2011 |
| WO | WO 2013/010910 | A1 | 1/2013 |
| WO | WO 2013/132091 | A1 | 9/2013 |
| WO | WO-2013132091 | A1 * | 9/2013 ......... A61B 1/00096 |
| WO | WO 2018/168635 | A1 | 9/2018 |

OTHER PUBLICATIONS

Extended European Search Report dated Jun. 8, 2021 in European Patent Application No. 211516398, 8 pages.
Combined Chinese Office Action and Search Report dated Dec. 17, 2021 in Chinese Patent Application No. 2021100492519 (with unedited computer generated Engiish translation), 15 pages.
Japanese Office Action dated Jun. 21, 2022 in Japanese Patent Appiication No. 2020-004242 (with unedited computer generated English translation), 12 pages.
Notice of Patent Grant dated Jan. 2, 2024, issued in counterpart CN Application No. 2022104458973, with machine English translation and search report, citing document No. 15-17. (9 pages).

* cited by examiner

CAP, IMAGE CAPTURING DEVICE, DATA GENERATION SYSTEM, AND DATA GENERATION METHOD

BACKGROUND

Field

The present disclosure relates to a cap to be mounted on a light entrance of an image capturing device, an image capturing device with the cap mounted thereon, a data generation system, and a data generation method.

Description of the Background Art

In the field of dentistry, it has been done to obtain the shape of a tooth (teeth) by means of an image capturing device (intraoral scanner), and digitally design a prosthesis or the like on a computer based on data of the obtained three-dimensional shape (also referred to as data, or 3D data) of the tooth (teeth). Japanese Patent No. 5654583 discloses a handheld intraoral scanner that uses the technique of the focus method to obtain the three-dimensional shape of a tooth (teeth). Specifically, this intraoral scanner projects light having a line or checkerboard pattern (hereinafter also referred to as pattern) onto a tooth (teeth), and determines, from a captured image of the projected pattern, the focus distance to thereby obtain the three-dimensional shape of the tooth (teeth).

On the intraoral scanner, a cap (also referred to as tip) is mounted for capturing an image of the inside of the oral cavity, and the intraoral scanner captures an image of a pattern projected onto a tooth (teeth) from a light inlet of the cap. The cap has a tubular housing that is easy to be inserted into an oral cavity, and a mirror disposed in the housing, and an image of a pattern projected from the light inlet of the housing is captured.

SUMMARY

The intraoral scanner is designed with the aim of capturing an image of the three-dimensional shape of a tooth (teeth), and therefore, the depth-of-field is defined so as to focus on the tooth (teeth) to be imaged. Specifically, the top end of a cap of the intraoral scanner is held along the row of teeth, and then the intraoral scanner captures the shape of the tooth (teeth). Therefore, the depth-of-field is defined in the vicinity of the light inlet of the cap.

The intraoral scanner thus lacks flexibility in the depth-of-field to be imaged and, in some cases, it has been difficult to fully obtain the shape of teeth that may vary depending on individuals and/or depending on teeth conditions such as partial or missing teeth. Although the depth-of-field can be changed by an optical mechanism provided in the intraoral scanner, the optical mechanism provided for changing the depth-of-field increases the size of the housing, which may hinder intraoral imaging.

The present disclosure is given to provide solutions to the above problems, and an object of the disclosure is to provide a cap, an image capturing device, a data generation system, and a data generation method that can give flexibility to the depth-of-field to be imaged, without increasing the size of the image capturing device.

A cap according to the present disclosure is a cap mountable on and detachable from an image capturing device, and the cap includes: a housing having an opening for connecting to at least a part of the image capturing device; a light inlet provided in the housing and located opposite to the opening; and a reflector that reflects light from the light inlet toward the opening, and the housing has a longitudinal length shorter than that of a cap defining a depth-of-field, of the image capturing device, extending from the light inlet to a predetermined extent.

An image capturing device according to the present disclosure includes the above-described cap and a connector connected detachably to the cap.

A data generation system according to the present disclosure is a data generation system including: an image capturing device that obtains, as data, a shape of a tooth in an oral cavity; and a data generator that generates data for producing a prosthesis. The image capturing device obtains three-dimensional data of a tooth including an occlusal portion, with a first cap mounted to define a depth-of-field of the image capturing device that extends from a light inlet of the first cap to a predetermined extent, or with a cap mounted at a first position defining a depth-of-field of the image capturing device that extends from the light inlet of the cap to the predetermined extent. The image capturing device obtains three-dimensional data of a tooth where the occlusal portion is missing and a portion extending from the occlusal portion toward an alveolar bone remains, with a second cap mounted to define a depth-of-field of the image capturing device that extends from a position away from the light inlet of the second cap to the predetermined extent, or with a cap mounted at a second position defining a depth-of-field of the image capturing device that extends from a position away from the light inlet of the cap to the predetermined extent. The data generator generates data for producing a prosthesis that at least includes a portion to be brought into contact with the tooth where the occlusal portion is missing and the portion extending from the occlusal portion toward the alveolar bone remains, based on the three-dimensional data of the tooth including the occlusal portion and the three-dimensional data of the tooth where the occlusal portion is missing and a portion extending from the occlusal portion toward the alveolar bone remains, obtained by the image capturing device.

A data generation method according to the present disclosure is a data generation method of generating data by a data generation system for producing a prosthesis. The data generation system includes: an image capturing device that obtains, as three-dimensional data, a shape of a tooth in an oral cavity; and a data generator that generates data for producing a prosthesis. The method includes: obtaining data of a tooth including an occlusal portion, by the image capturing device with a first cap mounted to define a depth-of-field of the image capturing device that extends from a light inlet of the first cap to a predetermined extent, or with a cap mounted at a first position defining a depth-of-field of the image capturing device that extends from the light inlet of the cap to the predetermined extent; obtaining data of a tooth where the occlusal portion is missing and a portion extending from the occlusal portion toward an alveolar bone remains, by the image capturing device with a second cap mounted to define a depth-of-field of the image capturing device that extends from a position away from the light inlet of the second cap to the predetermined extent, or with a cap mounted at a second position defining a depth-of-field of the image capturing device that extends from a position away from the light inlet of the cap to the predetermined extent; and generating data for producing a prosthesis that at least includes a portion to be brought into contact with the tooth where the occlusal portion is missing and the portion extending from the occlusal portion toward the alveolar bone remains, based on the three-dimensional data of the tooth including the occlusal portion and the three-dimensional data of the tooth where the occlusal portion is missing and the portion extending from the occlusal portion toward the alveolar bone remains, obtained by the image capturing device.

The foregoing and other objects, features, aspects and advantages of the present disclosure will become more apparent from the following detailed description of the present disclosure when taken in conjunction with the accompanying drawings.

DESCRIPTION OF THE PREFERRED EMBODIMENTS

Embodiments are described hereinafter with reference to the drawings.

Embodiment 1

An image capturing device according to Embodiment 1 is an intraoral sauna for obtaining the three-dimensional shape of a tooth (teeth) in the oral cavity. The image capturing device according to the present disclosure, however, is not limited to the intraoral scanner, but may be a scanner that is an image capturing device having a similar configuration. For example, it may be a scanner capable of capturing an image of the inside of a human ear, besides the inside of the oral cavity, to obtain the shape of the inside of the external ear.

Figure 1:
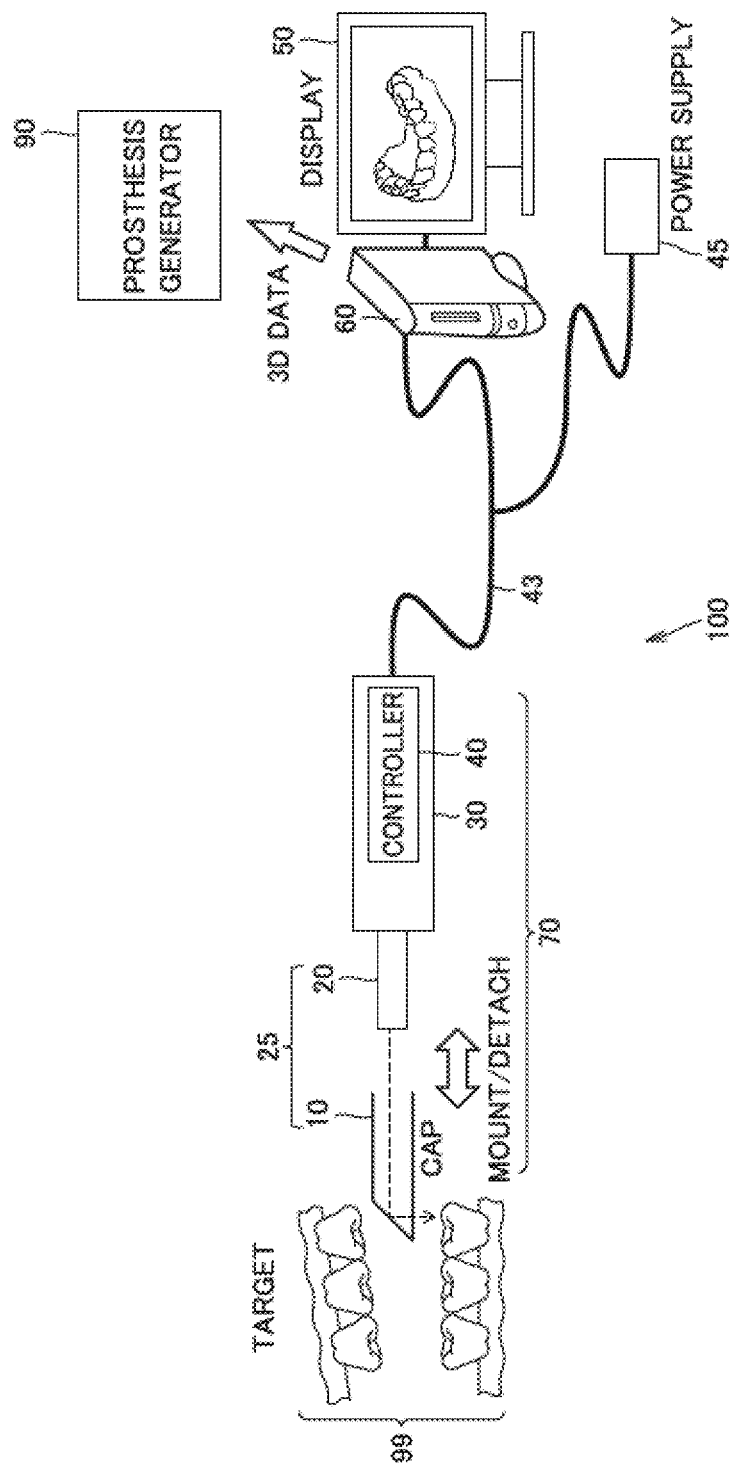
FIG. 1 is a block diagram showing a configuration of an intraoral scanner according to Embodiment 1.

[Configuration of Intraoral Scanner] FIG. 1 is a block diagram showing a configuration of an intraoral scanner 100 according to Embodiment 1. As shown in FIG. 1, intraoral scanner 100 includes a cap (also referred to as tip) 10, a tubular portion 20, a housing 30, a controller 40, a power supply 45, a display 50, and a processor 60. Processor 60 is configured as an information processor such as PC (personal computer), for example, and illustration in drawings and description of components such as PC power supply, data communication module, and mouse, for example, that are less relevant to the present disclosure are not given herein. Power supply 45, display 50, and processor 60 are connected by a cable 43 to a hand piece 70 that includes cap 10, tubular portion 20, housing 30, and controller 40. Hand piece 70 alone may also be referred to as intraoral scanner. Intraoral scanner 100 transmits data of the obtained three-dimensional shape (also refaced to as three-dimensional data) of a tooth (teeth) to processor 60, and processor 60 performs processing an the data.

The data transmitted to processor 60 is a plurality of pieces of data obtained by successively imaging a target 99 from different positions. Processor 60 is capable of performing registration processing to connect these data pieces into data of the whole dental arch or a part of the dental arch. Moreover, processor 60 performs, in addition to the registration processing an operation of applying calibration information to intraoral scanner 100, an operation of rendering the three-dimensional data generated by the registration processing, so that target 99 to be displayed on display 50 appears three-dimensionally, and an operation of storing, in a storage, tare-dimensional data transmitted to the processor and the three-dimensional data generated by the registration processing, for example. Processor 60 includes, as hardware components, a CPU (Central Processing Unit) for performing the above-described operations, the storage for storing programs and data for example for causing the operations to be performed by the CPU, a RAM (Random Access Memory) serving as a work area for the CPU, a GPU (Graphics Processing Unit) that chiefly performs image processing, and an input/output interface for ensuring signal consistency with peripherals, for example. Examples of the storage include a storage device such as hard disk mounted ted in processor 60, a storage device connected through a network, and the like.

Further, in order to design a prosthesis that fits on a partially-missing tooth of the three-dimensional data, processor 60 can execute a program (CAD program) to design the prosthesis from the data resultant from the registration processing. The CAD program may be executed by another PC or the like connected through a network, rather than by processor 60, to design the prosthesis from the three-dimensional data resultant from the registration processing by the other PC. As the CAD program, known dental CAD software or the like may be provided for example and installed so that processor 60 can execute the software.

Processor 60 can execute the CAD program to generate data for producing a prosthesis that includes at least a portion to be brought into contact with a tooth where its original occlusal portion is missing and a portion extending from the originally present occlusal portion toward the alveolar bone remains, based on data of the tooth including the occlusal portion and three-dimensional data of the tooth where the occlusal portion is missing and the portion extending from the occlusal portion toward the alveolar bone remains that are obtained by means of intraoral scanner 100. In other words, processor 60 can use the CAD program to generate data of the three-dimensional shape of a prosthesis (prosthesis design data), from the three-dimensional data resultant from the registration processing. Processor 60 operates as a data generator that executes the CAD program to generate prosthesis design data for producing a prosthesis. Processor 60 can send the generated prosthesis design data to a prosthesis producer 90. Data may be transmitted from processor 60 to prosthesis producer 90 through communication such as wireless communication or wired communication, or through copying via a memory or the like. Prosthesis producer 90 is, for example, a milling machine or 3D printer, and produces a prosthesis for a partially-missing tooth (teeth) based on the received prosthesis design data. Intraoral scanner 100 may incorporate processor 60 which executes the CAD program, to thereby form a data generation system. When prosthesis producer 90 executes the CAD program, a system including intraoral scanner 100 and prosthesis producer 90 may be referred to as data generation system.

While processor 60 is described as being provided as a PC which is separate from hand piece 70, processor 60 is not limited to this but may be configured as a CPU incorporated in hand piece 70, a processor mounted at a middle position of cable 43, a processor on the cloud, or the like. Moreover, while the CAD program is described as being executed by processor 60, what executes the CAD program is not limited to processor 60 but may be a CPU incorporated in hand piece 70, a processor mounted at a middle position of cable 43, a CPU incorporated in prosthesis producer 90, a processor on the cloud, or the like. In other words, the prosthesis design data may be generated by a CPU incorporated in hand piece 70, a processor mounted at a middle position of cable 43, a CPU incorporated in prosthesis producer 90, a processor on the cloud, or the like.

Further, the CAD program may be a program that can use an AI (artificial intelligence) engine capable of machine learning such as deep learning. The CAD program may use the AI engine to automatically design a prosthesis based on a trained model, from information about the patient (such as age, sex), and information about characteristics of an opposing tooth (teeth) and adjacent tooth (teeth) extracted from the three-dimensional data resultant from the registration processing, for example.

Prosthesis producer 90 may produce a prosthesis, not from the prosthesis design data generated by means of the CAD program, but from three-dimensional data that is generated through imaging by intraoral scanner 100 and directly input to prosthesis producer 90. Further, prosthesis producer 90 may not produce a prosthesis but produce a model of an imaged row of teeth, based on three-dimensional data generated through imaging by intraoral scanner 100, and the model may be used for giving explanation to a patient (for counselling), making surgery planning, designing dental braces, checking whether a prosthesis fits, or checking occlusal movement, for example.

Cap 10 is inserted in an oral cavity in which target 99 is located, projects light having a pattern (also referred to as "pattern" hereinafter) onto target 99, and directs the reflected light from target 99 on which the pattern is projected, to tubular portion 20 and housing 30. Moreover, cap 10 is mountable on and detachable from tubular portion 20, and therefore, only cap 10 which may be brought into contact with a living organism can be detached from tubular portion 20 to be subjected to sterilization (subjected to autoclave treatment in a high-temperature high-humidity environment, subjected to dry heat sterilization, or immersed in a medical solution, for example) for preventing infection. Cap 10 is made up of a mirror and housing 12 that holds the music at one end and covers tubular portion 20 at the other end.

Tubular portion 20 has a shape that can be fit in cap 10, and protrudes from housing 30. Tubular portion 20 includes an optical component(s) such as relay lens, polarizer, optical filter, optical window, and waveplate ($\lambda/4$ plate or the like), for directing light received by cap 10 to housing 30. Cap 10 and tubular portion 20 constitute a probe 25. Tubular portion 20 may be a part of housing 30 or a part separate from housing 30.

Housing 30 projects a pattern on target 99 through cap 10 and captures an image of the projected pattern. Housing 30 includes an optical component and a light source for generating a pattern to be projected on target 99, a lens component for focusing the pattern on the surface of target 99, a focus adjustment mechanism for adjusting the focus of the lens, and an image capturing device for capturing an image of the projected pattern, for example. Housing 30 is described herein as being configured to obtain a shape by the technique of the focus method. Housing 30, however, is not limited to this configuration but may be configured to acquire a three-dimensional shape by a technique such as confocal method, triangulation, white light interferometry, stereo method, photogrammetry, SLAM (Simultaneous Localization and Mapping), or optical coherence tomography (OCT). In other words, housing 30 configured on the basis of any principle is applicable as long as it is configured to acquire a three-dimensional shape by an optical technique.

Controller 40 is contained in housing 30 controls respective operations of mechanical parts and electronic parts disposed in housing 30, and transmits, to processor 60, the data resultant from the imaging. Controller 40 includes a CPU (Central Processing Unit) as a control center, a ROM (Read Only Memory) storing programs and control data for example for the CPU to operate, a RAM (Random Access Memory) serving as a work area for the CPU, a GPU (Graphics Processing Unit) that chiefly performs image processing, and an input/output interface for ensuring signal consistency with peripherals, for example. The CPU and/or the GPU may be configured in the form of an FPGA (Field Programmable Gate Array). Controller 40 may be configured to perform processing of processor 60 and, when controller 40 can perform processing of processor 60, controller 40 is able to directly output the three-dimensional data to display 50. Further, controller 40 may enable information such as settings for housing 30 to be input by an input device or the like (not shown).

It should be noted that while operations such as registration processing and application of calibration information to intraoral scanner 100 are described herein as being implemented through execution of software by processor 60 or controller 40, this is not a limitation. Alternatively, it may be implemented by hardware that is dedicated to the aforementioned operations. The hardware may be contained in housing 30 or located at a middle position of cable 43. While FIG. 1 depicts components (30, 50, 45, 60) of intraoral scanner 100 as being connected to each other by cable 43, a part or the whole of the connection may be implemented by wireless communication. Alternatively, they may be connected to each other by an optical cable rather than an electrical cable. It should be noted that controller 40 may be provided as a component separate from housing 30, rather than being contained in housing 30, to thereby reduce the weight of hand piece 70.

Power supply 45 is a device for supplying electric power to drive housing 30 and controller 40. Power supply 45 may be mounted outside controller 40 as shown in FIG. 1, or mounted inside controller 40. Power supply 45 may include a plurality of power supplies so that electric power can be fed separately to housing 30 and display 50.

Display 50 is a display device for showing the resultant three-dimensional shape of target 99 obtained by controller 40. Display 50 can also be used as a display device for showing other kinds of information such as information about settings for housing 30, information about a patient, activation state of the scanner, manual, help screen, for example. As display 50, a stationary liquid crystal display, a head-mount display, or a glasses-type wearable device, for example, is applicable. Display 50 may be more than one display, and the results of measurement of the shape and/or other kinds of information may be displayed simultaneously or in the divided form on a plurality of displays 50.

Figure 2A:
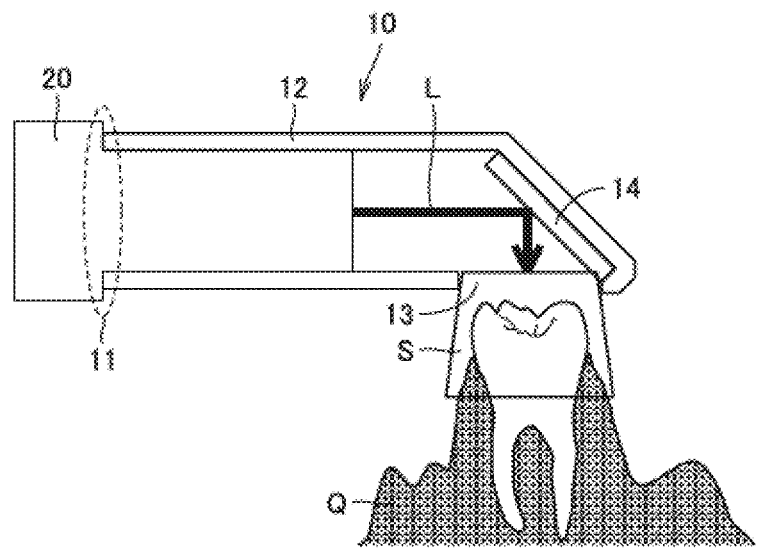
FIG. 2A is a schematic diagram for illustrating a configuration of a cap according to Embodiment 1.
Figure 2B:
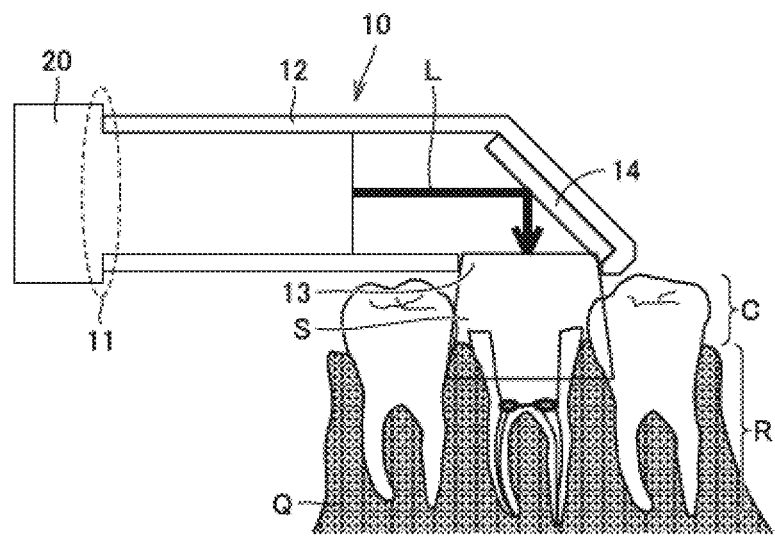
FIG. 2B is a schematic diagram for illustrating the configuration of the cap according to Embodiment 1.

[Configuration of Cap] Next, the configuration of cap 10 is described in further detail. FIGS. 2A and 2B are schematic diagrams for illustrating the configuration of cap 10 according to Embodiment 1. First, the configuration of cap 10 is described with reference to FIG. 2A. Cap 10 includes a housing 12 having an opening 11 for connecting to tubular portion 20, a measurement window 13 (light inlet) provided in housing 12 and located opposite to opening 11, and a mirror 14 (reflector) that directs light from measurement window 13 toward opening 11. Opening 11 is a hole far receiving tubular portion 20 to be inserted.

When cap 10 is mounted on tubular portion 20, the depth-of-field S of intraoral scanner 100 is defined from measurement window 13 of cap 10 to a predetermined extant. The predetermined extent of the depth-of-field S is an extent that includes a tooth (teeth) to be imaged. The longitudinal length of housing 12 is determined so that an optical path L from the top end of tubular portion 20 to the depth-of-field S is constant when cap 10 is mounted on tubular portion 20. It is therefore possible for intraoral scanner 100 to capture an image of the shape of the tooth (teeth) by mounting cap 10 on tubular portion 20 and holding cap 10 along the row of teeth. The depth-of-field S of intraoral scanner 100 is defined here to extend from measurement window 13 formed in the surface of housing 12 to a predetermined extent, as shown in FIG. 2A. Depending on any factor such as the position at which mirror 14 is attached, for example, the depth-of-field S of intraoral scam 100 may extend from the inside of mead window 13. Therefore, the depth-of-field S of intraoral scanner 100 may extend, not from the position of measurement window 13 formed in the surface of housing 12, but from any position near measurement window 13 to a predetermined extent. Cap 10 is referred to herein as a standard cap.

When a tooth to be imaged is a healthy tooth having no missing part, the depth-of-field S of immoral scanner 100 includes the tooth to be imaged, as shown in FIG. 2A. However, when a tooth to be imaged is a partially misusing tooth where a tooth portion C including the occlusal surface is missing and only a root canal portion R remains (for example, when a tooth shaped to expose the root canal for root canal treatment is to be scanned), the depth-of-field S of intraoral scanner 100 is hindered by adjacent teeth and thus cannot encompass the partially-missing tooth, as shown in FIG. 2B. In order to capture an image of the partially-missing tooth, the depth-of-field S of intraoral scanner 100 may be enlarged. If the depth-of-field S of intraoral scanner 100 is enlarged, a movable object Q (tongue and/or mucous membrane, for example) is additionally imaged, resulting in increase of the risk of failure in the registration processing of a plurality of pieces of data to be united into data of the three-dimensional shape. While the movable object Q may be removed by arithmetic operation from the data of the imaged three-dimensional shape, the load of the arithmetic operation by controller 40 and processor 60 increases. Further, if an optical mechanism is provided in unmoral scanner 100 for enlarging the depth-of-field S, the size of the housing is accordingly increased and/or the production cost is increased. In particular, a movable range for a plane to be focused should be large in order to increase the depth-of-field of the intraoral scanner using the focus method, which increases the size of a motor for moving an optical element for focusing.

Figure 3:
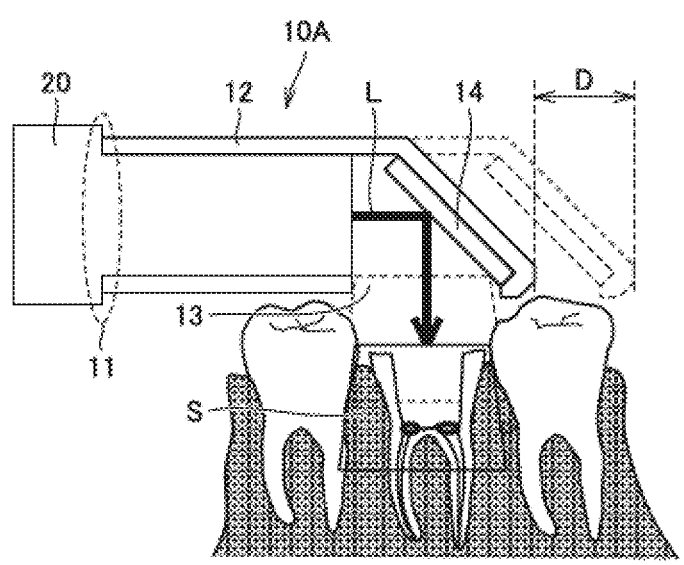
FIG. 3 is a schematic diagram for illustrating a configuration of a cap having a housing with a shorter longitudinal length among caps according to Embodiment 1.

In view of die above, in intraoral scanner 100 according to the present embodiment, a cap is mounted that has a shorter longitudinal length of housing 12 than that of cap 10 to be used for imaging a healthy tooth with no missing part. The longitudinal length of housing 12 herein refers to the length that directly influences the optical path length from opening 11 to mirror 14. Therefore, a mere change of the dimensions of the external shape that does not change the optical path length from opening 11 to mirror 14 is not included in "change of the longitudinal direction of housing 12" herein. FIG. 3 is a schematic diagram for illustrating a configuration of a cap 10A having a shorter longitudinal length of housing 12, among caps according to Embodiment 1.

When cap 10A is mounted on tubular portion 20, the depth-of-field S of intraoral scanner 100 is defined to extend from a position away from measurement window 13 of cap 10A to a predetermined ems. As shown in FIG. 3, the depth-of-field S extends from a position away from measurement window 13, and therefore, the root canal portion located further from measurement window 13 can be imaged.

When cap 10A is mounted an tubular portion 20, the optical path length L from the top end of tubular portion 20 to the depth-of-field S is identical to that of cap 10. Cap 10A, however, has the longitudinal length of housing 12 that is shatter by a distance D than that of cap 10. Cap 10 is shown in FIG. 3 by broken lines. Accordingly, when cap 10A is mounted on inimical scanner 100, the position of the depth-of-field S is shifted away from measurement window 13 by the distance by which the longitudinal length of housing 12 of cap 10A is shorter than that of cap 10. Then, intraoral scanner 100 with cap 10A mounted on tubular portion 20 can capture an image of the three-dimensional shape of a partially tooth where a tooth portion C is missing and only a root canal portion R remains, by holding cap 10A along the row of teeth. Namely, for such missing conditions, cap 10A may be regarded as a cap adapted to the root canal.

Figure 4:
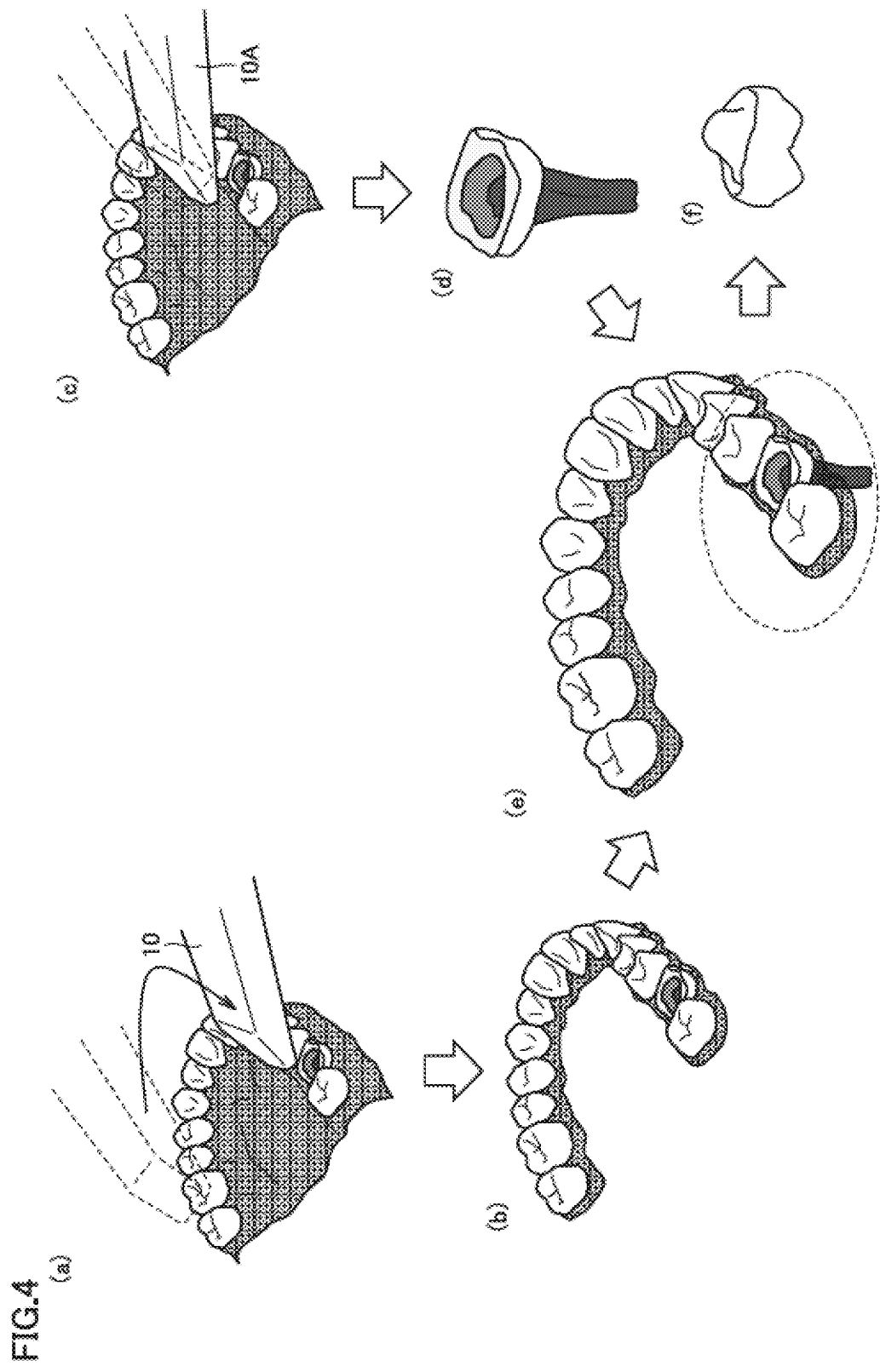
FIG. 4 illustrates a method of producing a prosthesis from an image, captured by an immoral scanner, of a three-dimensional shape of a dental arch including a partially-missing tooth.

Intraoral scanner 100 can capture an image of the three-dimensional shape of a dental arch that includes a partially-missing tooth, by replacing cap 10 having a relatively longer longitudinal length of housing 12 and cap 10A having a relatively shorter longitudinal length of housing 12 with each other so as to use an appropriate one. The shape of the dental arch including a partially-missing tooth can be obtained to produce a prosthesis that is most suitable for the partially-missing tooth. A specific method of capturing, by means of intraoral scanner 100, an image of the shape of a dental arch including a partially-missing tooth, to thereby produce a prosthesis is described with reference to a drawing. FIG. 4 illustrates a method of capturing, by means of intraoral scanner 100, an image of the shape of a dental arch including a partially-missing tooth, to thereby produce a prosthesis.

Initially, referring to FIG. 4 (a), intraoral scanner 100 on which cap 10 is mounted is moved along a dental arch to capture an image of the dental arch FIG. 4 (b) is data of the shape of the dental arch obtained as a result of the imaging illustrated in FIG. 4 (a). While the data of the three-dimensional shape of FIG. 4 (b) includes data of the shape of the teeth including the occlusal portion, it does not include data of the shape of a deep portion (root canal portion, for example) of the partially-missing tooth.

Then, referring to FIG. 4 (c), intraoral scanner 100 on which cap 10A is mounted is used to capture an image of a region including the partially-missing tooth. FIG. 4 (d) is data of the shape of the partially missing tooth obtained as a result of the imaging illustrated in FIG. 4 (c). The data of the shape of FIG. 4 (d) includes data of the shape of the deep portion (root canal portion, for example) of the partially-missing tooth.

FIG. 4 (e) is data of the shape of the dental arch that is a combination of the data of the three-dimensional shape of FIG. 4 (b) and the data of the three-dimensional shape of FIG. 4 (d). The data of the three-dimensional shape of FIG. 4 (e) includes both the data of the three-dimensional shape of the teeth including the occlusal portion and the data of the shape of the deep portion (root canal portion, for example) of the partially-missing tooth. The data of the three-dimensional shape of FIG. 4 (e) is used to produce, by prosthesis producer 90 shown in FIG. 1, a prosthesis (FIG. 4 (f)) that is most suitable for the partially-missing tooth. As a method of obtaining the three-dimensional shape data of FIG. 4 (e) by combining the three-dimensional shape data of FIG. 4 (b) and the three-dimensional shape data of FIG. 4 (d), a known method such as ICP (Iterative Closest Point) algorithm may be used. Specifically, coordinate adjustments may be made so that, in the region common to the three-dimensional shape data of FIG. 4 (b) and the three-dimensional shape data of FIG. 4 (d), the coordinates substantially overlap to the maximum extent, to thereby obtain the three-dimensional shape data of FIG. 4 (e).

Thus, cap 10A according to Embodiment 1 is a cap that is mountable on and detachable from immoral scanner 100. Cap 10A includes housing 12 having opening 11 for connecting to at least a part of intraoral scanner 100, measurement window 13 provided in housing 12 and located opposite to opening 11, and mirror 14 that reflects light from measurement window 13 toward opening 11. Housing 12 has a longitudinal length shorter than that of a probe defining a depth-of-field, of intraoral scanner 100, extending from measurement window 13 to a predetermined extent. Accordingly, cap 10A can shill the depth-of-field S to a position away from measurement window 13, to give flexibility to the depth-of-field S to be imaged, without increasing the size of intraoral scanner 100. Therefore, Unmoral scanner 100 on which cap 10A is mounted can obtain data of the shape of a deep portion (root canal portion, for example) of a partially-missing tooth.

Intraoral scanner 100 is a scanner that obtains, as three-dimensional data, the shape of a tooth (teeth) in an oral cavity. Intraoral scanner 100 includes tubular portion 20 connected detachably to cap 10, 10A.

Further, intraoral scanner 100 with cap 10 (first cap) mounted thereon obtains three-dimensional data of a tooth (teeth) including the occlusal portion, and intraoral scanner 100 with cap 10A (second cap) mounted thereon obtains data of a tooth where the occlusal portion is missing and a portion extending from the occlusal portion toward the alveolar bone remains. In this way, intraoral scanner 100 can obtain the data of the shape of the shallower tooth portion as well as the data of the three-dimensional shape of the deeper tooth portion.

A data generation system includes intraoral scanner 100 that obtains, as three-dimensional data, a shape of a tooth in an oral cavity, and a data generator that generates data for producing a prosthesis. It should be noted that the data generator includes processor 60 that executes a CAD program and prosthesis producer 90 that executes the CAD program for example. Intraoral scanner 100 obtains three-dimensional data of a tooth including an occlusal portion, with cap 10 (first cap) mounted to define a depth-of-field of intraoral scanner 100 that extends from measurement window 13 of the cap to a predetermined extent, and obtains three-dimensional data of a tooth where the occlusal portion is missing and a portion extending from the occlusal portion toward an alveolar bone remains, with cap 10A (second cap) mounted to define a depth-of-field of intraoral scanner 100 that extends from a position away from measurement window 13 of the cap to the predetermined extent. Based on the data of the tooth including the occlusal portion obtained by intraoral scanner 100 and the three-dimensional data of the tooth where the occlusal portion is missing and the portion extending from the occlusal portion toward the alveolar bone remains that are obtained by intraoral scanner 100, the data generator generates data for producing a prosthesis that at least includes a portion to be brought into contact with the tooth where the occlusal portion is missing and the portion extending from the occlusal portion toward the alveolar bone remains. Thus, the data generation system can produce a prosthesis in consideration of the three-dimensional data of the partially-missing tooth, and can thus produce the prosthesis that is most suitable for the tooth.

A data generation method of generating data by a data generation system for producing a prosthesis includes the following steps: obtaining three-dimensional data of a tooth including an occlusal portion, by intraoral scanner 100 with cap 10 (first cap) mounted to define a depth-of-field of intraoral scanner 100 that extends from measurement window 13 of the cap to a predetermined extent; obtaining three-dimensional data of a tooth where the occlusal portion is missing and a portion ending from the occlusal portion toward an alveolar bone remains, by intraoral scanner 100 with cap 10A (second cap) mounted to define a depth-of-field of intraoral scanner 100 that extends from a position away from measurement window 13 of the cap to the predetermined extent; and generating, by the data generator, data far producing a prosthesis that at least includes a portion to be brought into contact with the tooth where the occlusal portion is missing and the portion extending from the occlusal portion toward the alveolar bone remains, based on the data of the tooth including the occlusal portion and the three-dimensional data of the tooth where the occlusal portion is missing and the portion extending from the occlusal portion toward the alveolar bone remains, obtained by intraoral scanner 100.

Embodiment 2

According to Embodiment 1, caps 10, 10A that are different from each other in the longitudinal length of housing 12 are prepared and these caps 10, 10A are replaced with each other to shift the position of the depth-of-field S of intraoral scanner 100. According to Embodiment 2, a configuration is described in which the same cap is used and a variable mechanism is provided that varies the position where the cap is mounted on the intraoral scanner so as to enable the position of the depth-of-field of the intraoral scanner to be shifted. Regarding Embodiment 2, components of the cap, the intraoral scanner, and the data generation system identical to those described in connection with Embodiment 1 are denoted by the same reference characters, and the detailed description is not repeated herein.

Figure 5:
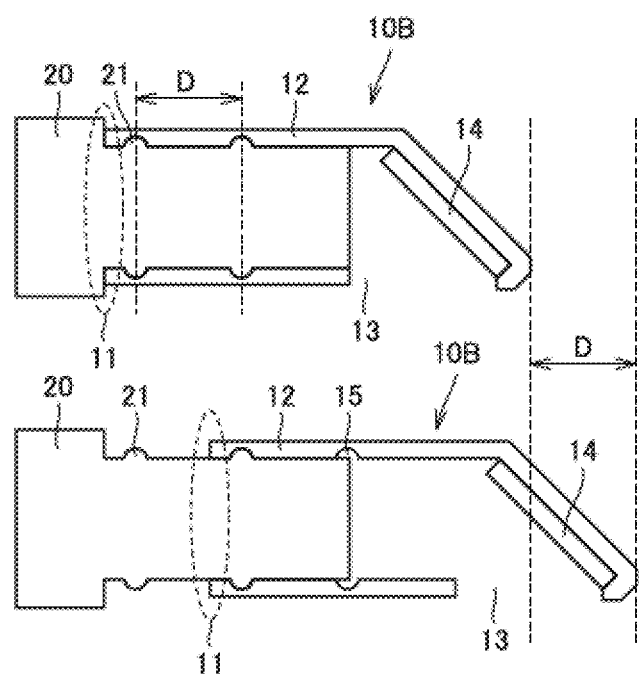
FIG. 5 is a schematic diagram showing a first example of the configuration of the cap according to Embodiment 2.

FIG. 5 is a schematic diagram showing a first example of a configuration of a cap according to Embodiment 2. Cap 10B shown in FIG. 5 has, as a variable mechanism, two grooves 15 in the inner wall of housing 12. One groove 15 is located relatively closer to opening 11, and the other groove 15 is located relatively further from opening 11. Tubular portion 20 of immoral scanner 100 has protrusions 21 corresponding to grooves 15.

Groove 15 and protrusion 21 can fit each other to fix the position of cap 10B with respect to tubular portion 20. Therefore, when cap 10B is mounted on tubular portion 20 at a position (second position) where two sets of grooves 15 and protrusions 21 fit each other, i.e., groove 15 and protrusion 21 of one set fit each other and groove 15 and protrusion 21 of the other set fit each other late the upper one in FIG. 5, the distance from the top end of tubular portion 20 to mirror 14 is reduced so that the position of the depth-of-field can be shifted away from measurement window 13 by the reduction of the optical path from the tubular portion 20 to mirror 14.

In contrast, like the lower one in FIG. 5, cap 10B is moved by a distance D in the longitudinal direction of housing 12 and mounted on tubular portion 20 at a position (first position) where groove 15 and protrusion 21 of one set fit each other. In this case, the distance from tubular portion 20 to mirror 14 is increased, and the position of the depth-of-field can be shifted toward measurement window 13 by the increase of the optical path from the top end of tubular portion 20 to mirror 14.

The configuration of grooves 15 and protrusions 21 shown in FIG. 5 is given by way of example, and the shape of grooves 15 and protrusions 21 is not limited to the shape shown in FIG. 5. Moreover, grooves 15 may be formed in tubular portion 20 and protrusions 21 may be formed on cap 10B. Further, the number of grooves 15 and protrusions is not limited to two sets of grooves and protrusions, and more grooves 15 and more protrusions 21 may be formed.

Figure 6:
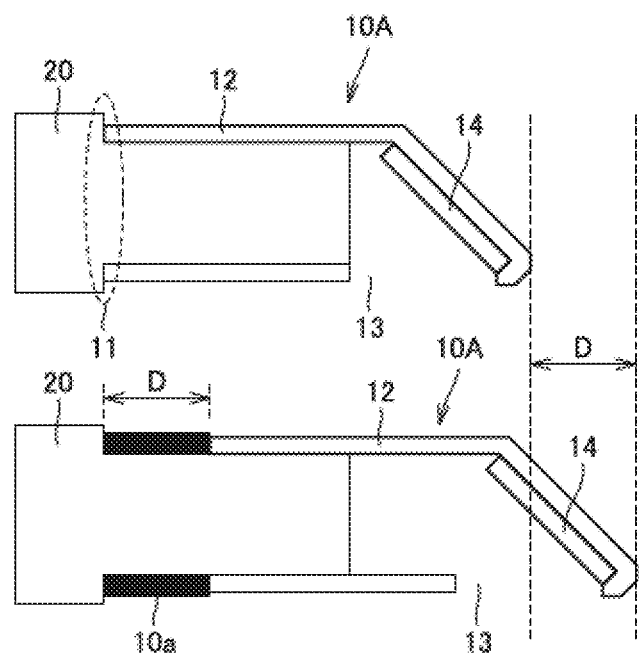
FIG. 6 is a schematic diagram showing a second example of the configuration of the cap according to Embodiment 2.

Next, FIG. 6 is a schematic diagram showing a second example of the configuration of the cap according to Embodiment 2. Cap 10A shown in FIG. 6 includes, as a variable mechanism, a spacer 10a attachable to cap 10A. Spacer 10a can be attached to the opening 11-side end of cap 10A to prolong the opening 11-side end of housing 12.

Thus, Lie the tipper one in FIG. 6, at the position (second position) of cap 10A to which spacer 10a is not attached, the distance from the top end of tubular portion 20 to mirror 14 is reduced, so that the position of the depth-of-field can be shifted away from measurement window 13 by the reduction of the optical path from tubular portion 20 to mirror 14.

In contrast, spacer 10a can be attached to cap 10A like the lower one of FIG. 6, so that cap 10A can be mounted an tubular portion 20 at the position (first position) where cap 10A itself is shifted by distance D in the longitudinal direction of housing 12. In this case, the distance from tubular portion 20 to mirror 14 is increased, so that the position of the depth-of-field can be shifted toward measurement window 13 by the increase of the optical path from the top end of tubular portion 20 to mirror 14.

The configuration of spacer 10a shown in FIG. 6 is given by way of eerie, and the shape of spacer 10a is not limited to the shape shown in FIG. 6. Moreover, spacer 10a may not be structured to be attached to cap 10A, and spacer 10a may only be arranged between cap 10A and tubular portion 20. Further, spacer 10a may not be a single piece, but may be a combination of many spacers. Specifically, a plurality of spacers (may differ from each other in length) may be used by being inserted between cap 10A and tubular portion 20, or a plurality of spacers 10a having different lengths may be prepared and at least one may be selected from them and used by being inserted between cap 10A and tubular portion 20.

Figure 7:
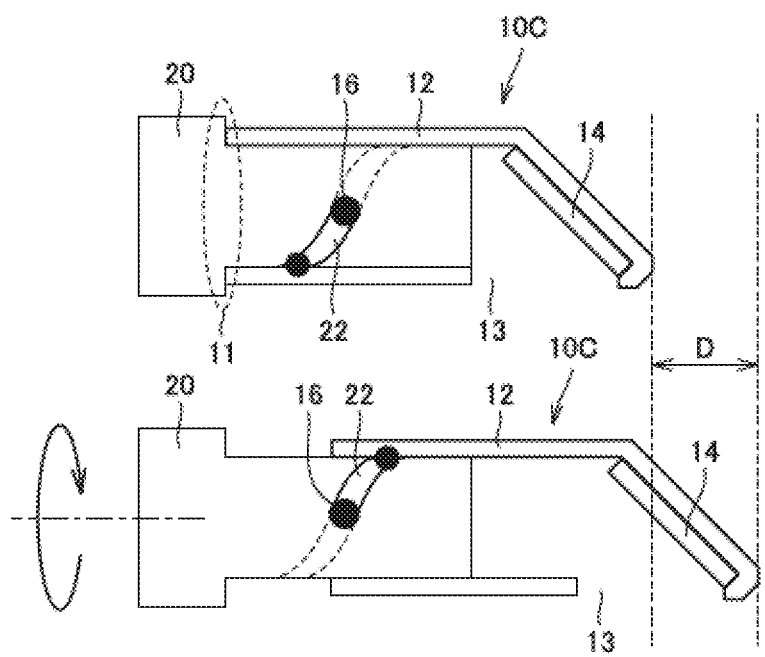
FIG. 7 is a schematic diagram showing a third example of the configuration of the cap according to Embodiment 2.

Next, FIG. 7 is a schematic diagram showing a third example of the configuration of the cap according to Embodiment 2_A cap 10C shown in FIG. 7 includes, as a variable mechanism, a rib 16 of a cam mechanism at the opening 11-side of housing 12. A groove 22 corresponding to rib 16 is provided in tubular portion 20 of intraoral scanner 100.

Groove 22 and rib 16 can fit each other to fix the position of cap 10C with respect to tubular portion 20. Therefore, when cap 10C is mounted on tubular portion 20 at a position (second position) where one rib 16 fits in groove 22 located at the opening 11-side like the upper one in FIG. 7, the distance from the top end of tubular portion 20 to mirror 14 is reduced so that the position of the depth-of-field can be shifted away from measurement window 13 by the reduction of the optical path from tubular portion 20 to mirror 14.

In contrast, like the lower one in FIG. 7, cap 10C is rotated with respect to tubular portion 20 and mounted on tubular portion 20 at a position (first position) where rib 16 originally located in groove 22 at the opening 11-side has been moved in the longitudinal direction of housing 12 by distance D. In this case, the distance from tubular portion 20 to mirror 14 is increased so that the position of the depth-of-field can be shifted toward merit window 13 by the increase of the optical path from the top end of tubular portion 20 to mirror 14.

The configuration of the cam mechanism shown in FIG. 7 is given by way of example, and the shape of the cam mechanism is not limited to the shape shown in FIG. 7. Moreover, as to the cam mechanism, rib 16 may be formed on tubular portion 20 and groove 22 may be formed in cap 10C. The cam mechanism may be replaced with an equivalent mechanism.

Figure 8:
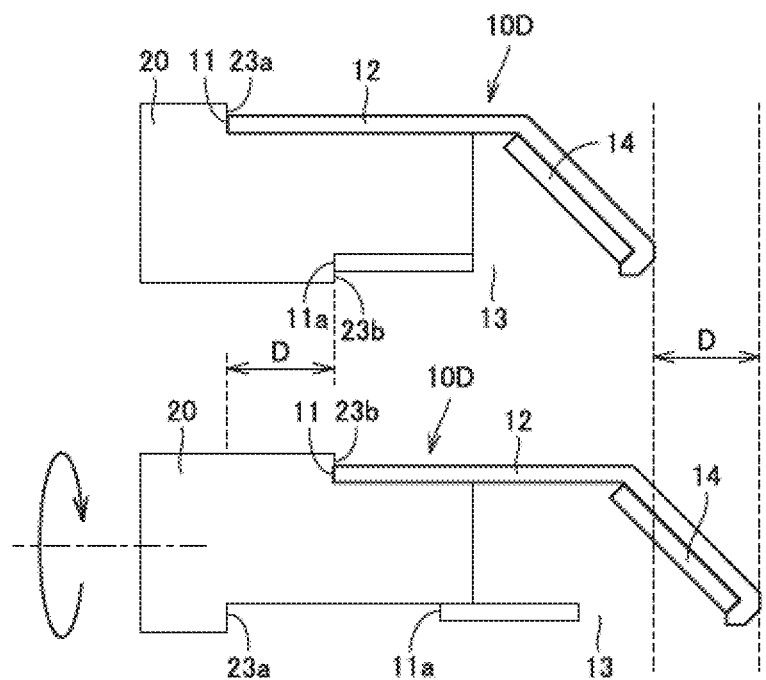
FIG. 8 is a schematic diagram showing a fourth example of the configuration of the cap according to Embodiment 2.

Next, FIG. 8 is a schematic diagram showing a fourth example of the configuration of the cap according to Embodiment 2. A cap 10D shown in FIG. 8 has, as a variable mechanism, a cut portion 11a formed in the end at opening 11. Tubular portion 20 of immoral scanner 100 includes walls 23a, 23b that are brought into contact, at different positions, with the end at opening 11 of cap 10D.

At the position where cut portion 11a is in contact with wall 23a, 23b, the position (second position) of cap 10D with respect to tubular portion 20 can be fixed. Therefore, like the upper one in FIG. 8, cap 10D is mounted on tubular portion 20 so that cut portion 11a is in contact with wall 23b. Then, the distance from the top end of tubular portion 20 to mirror 14 is reduced, and the position of the depth-of-field can be shifted away from measurement window 13 by the reduction of the optical path from tubular portion 20 to mirror 14.

In contrast, like the lower one in FIG. 8, cap 10D is rotated with respect to tubular portion 20 so that cap 10D is mounted on tubular portion 20 at the position (first position) where the end at opening 11 is in contact with wall 23b. Then, cap 10D itself can be moved by distance D in the longitudinal direction of housing 12 and mounted on tubular portion 20. The distance from tubular portion 20 to mirror 14 can be increased, so that the position of the depth-of-field can be shifted toward measurement window 13, by the increase of the optical path from the top end of tubular portion 20 to mirror 14.

The configuration of cut portion 11a shown in FIG. 8 is given by way of example, and the shape of cut portion 11a is not limited to the one shown in FIG. 8. The number of cut portions 11a famed in housing 12 is also not limited.

Thus, caps 10A to 10D according to Embodiment 2 are each a cap including: housing 12 having opening 11 for connecting to at least a pan of intraoral scanner 100, measurement window 13 provided in housing 12 and located opposite to opening 11, mirror 14 that reflects light from measurement window 13 toward opening 11, and a variable mechanism that allows the position where the cap is mounted on intraoral scanner 100 to be variable, so as to change the length of optical path L from the top end (light entrance) of tubular portion 20 to mirror 14. Accordingly, caps 10A to 10D can shift the depth-of-field S to a position away from measurement window 13, to give flexibility to the depth-of-field S to be imaged, without increasing the size of intraoral scanner 100. Therefore, intraoral scanner 100 on which cap 10A to 10D is mounted can obtain data of the shape of a deep portion (root canal portion, for example) of a partially-missing tooth.

The variable mechanism may be spacer 10a that extends from the opening 11-side of housing 12 to prolong the housing. The variable mechanism may be a plurality of grooves 15 or protrusions that are provided at respective different positions in the inner surface of housing 12 at the opening-11 side and that are to fit with intraoral scanner 100. The variable mechanism may be a groove or rib 16 of a cam mechanism formed at the opening 11-side of housing 12. The variable mechanism may be cut portion 11a formed in the end at opening 11, so that the position where cap 10D is brought into contact with intraoral scanner 100 varies depending an the orientation in which cap 10D is mounted.

Further, when cap 10A to 10D is mounted at the first position, intraoral scanner 100 obtains data of a tooth (teeth) including the occlusal portion. When cap 10A to 10D is mounted at the second position, intraoral scanner 100 obtains three-dimensional data of a tooth where its occlusal portion is missing and a portion extending from the occlusal portion toward the alveolar bone remains. Accordingly, intraoral scanner 100 can obtain the data of the three-dimensional shape of a shallower tooth portion as well as the data of the shape of a deeper tooth portion.

A data generation system includes intraoral scanner 100 that obtains, as three-dimensional data, a shape of a tooth in an oral cavity, and a data generator that generates data for producing a prosthesis. It should be noted that the data generator includes processor 60 that executes a CAD program and prosthesis producer 90 that executes the CAD program, for example. Intraoral scanner 100 obtains three-dimensional data of a tooth including an occlusal portion, with cap 10A to 10D mounted at the first position to define a depth-of-field of intraoral scanner 100 that extends from measurement window 13 of the cap to a predetermined extent, and obtains data of a tooth where the occlusal portion is missing and a portion extending from the occlusal portion toward an alveolar bone remains, with cap 10A to 10D mounted at the second position to define a depth-of-field of intraoral scanner 100 that extends from a position away from measurement window 13 of the cap to the predetermined extent. Based on the three-dimensional data of the tooth including the occlusal portion obtained by intraoral scanner 100 and the three-dimensional data of the tooth where the occlusal portion is missing and the portion extending from the occlusal portion toward the alveolar bone remains that are obtained by immoral scanner 100, the data generator generates data for producing a prosthesis that at least includes a portion to be brought into contact with the tooth where the occlusal portion is missing and the portion extending from the occlusal portion toward the alveolar bone remains. Thus, the data generation system can produce a prosthesis in consideration of the data of the partially-missing tooth, and can tins produce the prosthesis that is most suitable for the tooth.

A data generation method of generating data by a data generation system for producing a prosthesis includes the following steps: obtaining three-dimensional data of a tooth including an occlusal portion, by intraoral scanner 100 with cap 10A to 10D mounted at the first position to define a depth-of-field of intraoral scanner 100 that extends from measurement window 13 of the cap to a predetermined extent; obtaining three-dimensional data of a tooth where the occlusal portion is missing and a portion extending from the occlusal portion toward an alveolar bone remains, by intraoral scanner 100 with cap 10A to 10D mounted at the second position to define a depth-of-field of intraoral scanner 100 that extends from a position away from measurement window 13 of the cap to the predetermined extent and generating, by the data generator, data for producing a prosthesis that at least includes a portion to be brought into contact with the tooth where the occlusal portion is missing and the portion extending from the occlusal portion toward the alveolar bone remains, based on the three-dimensional data of the tooth including the occlusal portion and the three-dimensional data of the tooth where the occlusal portion is missing and the portion extending from the occlusal portion toward the alveolar bone remains, obtained by intraoral scanner 100.

Embodiment 3

According to Embodiment 1, caps 10, 10A different from each other in the longitudinal length of housing 12 are prepared and these caps 10, 10A are replaced with each other to shift the position of the depth-of-field S of intraoral scanner 100. According to Embodiment 3, a configuration is described in which a cap is selected and used from caps having the same length and equipped with an optical element in the housing of the cap so as to enable the position of the depth-of-field of the intraoral scanner to be shifted. Regarding Embodiment 3, components of the cap, the intraoral scanner, and the data generation system identical to those described in connection with Embodiment 1 are denoted by the same reference characters, and the detailed description is not repeated herein.

Figure 9A:
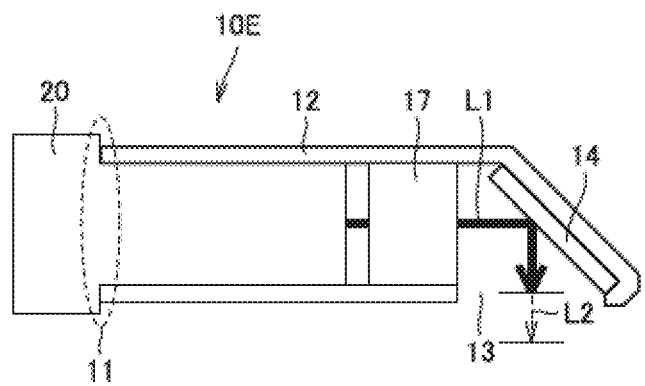
FIG. 9A is a schematic diagram showing an example of the configuration of the cap according to Embodiment 3.
Figure 9B:
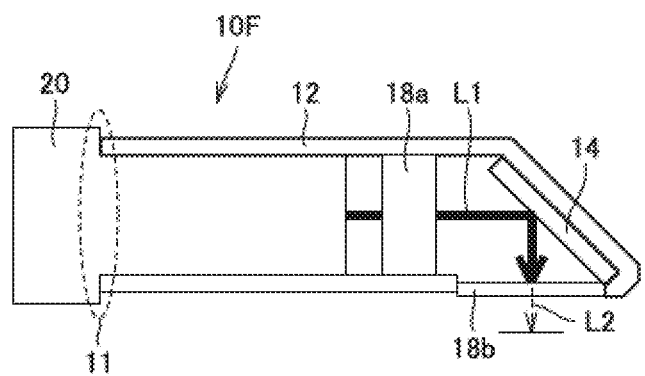
FIG. 9B is a schematic diagram showing an example of the configuration of the cap according to Embodiment 3.
Figure 9C:
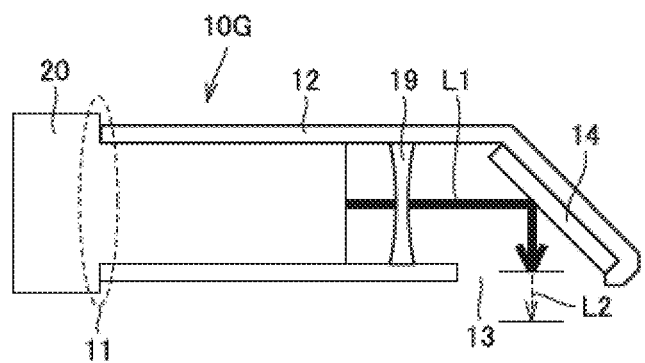
FIG. 9C is a schematic diagram showing an example of the configuration of the cap according to Embodiment 3

FIGS. 9A to 9C are each a schematic diagram showing an example of the configuration of the cap according to Embodiment 3. A cap 10E shown in FIG. 9A includes a flat glass plate (optical element) 17 with a refractive index n located on an optical path L1 extending from the top end of tubular patios 20 to measurement window 13. For intraoral scanner 100 making use of the principle of the focus method, for example, the presence of flat glass plate 17 on optical path L1 increases, by optical path L2, the focal distance that defines the depth-of-field, relative to the case where flat glass plate 17 is absent. Therefore, the depth-of-field of intraoral scanner 100 on which cap 10E is mounted is shifted away by optical path L2. The shift amount is calculated by an approximation expression: L2=(1−1/n)t, where t is the thickness of flat glass plate 17. If t=12 mm and refractive index n is 1.6, for example, the amount of shift of the depth-of-field caused by flat glass plate 17 is L2=4.5 mm. Flat glass plate 17 is given by way of example, and may be any material other than glass, as long as it is an optical element having refractive index n, such as optical plastic, transparent ceramic material, or optical crystal, for example.

Moreover, flat glass plate 17 is not limited to a single flat glass plate, but may be made up of a plurality of flat glass plates. When the optical element is made up of a plurality of flat glass plates, they may be arranged at different positions as shown in FIG. 9B. Ina cap 10F shown in FIG. 9B, a flat glass plate 18a with refractive index n is disposed on optical path L1 from the top end of tubular portion 20 to measurement window 13, and a flat glass plate 18b with refractive index n is disposed in measurement window 13. The total thickness of flat glass plate 18a and flat glass plate 18b may be set identical to the thickness of flat glass plate 17, so that the same shift amount of the depth-of-field can be achieved.

When a flat glass plate is disposed in the cap and the flat glass plate is thick, an image distortion arises due to the refraction effect. It is then necessary to perform, by intraoral scanner 100, an arithmetic operation for correcting the distortion. Specifically, controller 40 switches the control mode, depending on whether the cap in which a flat glass plate is disposed is mounted on interest scanner 100 or the cap in which no flat glass plate is disposed is mounted on intraoral scanner 100. It should be noted that the following operations performed by controller 40, such as switching of the control mode, may alternatively be performed by processor 60 rather than by controller 40. Controller 40 determines, by means of determination means described later herein, the type of the cap mounted on intraoral scanner 100, and the control mode is switched automatically to a control mode appropriate for the type of the mounted cap. For example, when a cap in which a flat glass plate is placed is mounted on intraoral scanner 100, controller 40 uses a calibration table A to generate data of the three-dimensional shape and, when a cap in which no flat glass plate is placed is mounted on intraoral scanner 100, controller 40 uses a calibration table B to generate data of the shape.

The optical element placed in the cap is not limited to the flat glass plate but may be a lens. In a cap 10G shown in FIG. 9C, a concave lens (negative lens) 19 is placed on optical path L1 extending from the top end of tubular portion 20 to measurement window 13. The presence of concave lens 19 on optical path L1 increases the optical path by optical path L2, relative to the case where no concave lens 19 is placed. Therefore, the depth-of-field of intraoral scanner 100 on which cap 10G is mounted is shifted away by the distance of optical path L2. A convex lens (positive lens) provided on optical path L1 reduces the optical path relative to the case where no convex lens is provided, which is not shown. Thus, the amount of shift of the position of the depth-of-field can be adjusted similarly to the flat glass plate, by selecting any of caps that are different from each other in terms of whether the lens is present or not, or different in terms of the uneven shape of the lens and mounting the selected cap on tubular portion 20.

When the lens is placed in the cap, the field of view of the image varies depending on the magnification of the lens. It is therefore necessary to perform, by intraoral scanner 100 (or processor 60), an arithmetic operation for correcting the difference in the field of view. Specifically, controller 40 switches the control mode depending on whether a cap in which the lens is placed is mounted on intraoral scanner 100 or a cap in which no lens is placed is mounted on intraoral scanner 100. Controller 40 determines the type of the cap mounted on intraoral scanner 100, by means of determination means described later herein, and the control mode is automatically switched to a control mode appropriate for the type of the mounted cap. For example, when a cap in which a concave lens is disposed is mounted on intraoral scanner 100, controller 40 uses a calibration table A to generate data of the three-dimensional shape. When a cap in which no lens is disposed is mounted on intraoral scanner 100, controller 40 uses a calibration table B to generate data of the three-dimensional shape. When a cap in which a convex lens is placed is mounted on intraoral scanner 100, controller 40 uses a calibration table C to generate data of the three-dimensional shape.

Thus, caps 10E to 106 according to Embodiment 3 are each a cap including: housing 12 having opening 11 for connecting to at least a part of immoral scanner 100, measurement window 13 provided in housing 12 and located opposite to opening 11, mirror 14 that reflects light from measurement window 13 toward opening 11, and an optical element (flat glass plate 17, 18a, 18b, concave lens 19) that causes the depth-of-field of intraoral scanner 100 to be shifted, so that the depth-of-field extends from a position away from measurement window 13 to a predetermined extent. Accordingly, caps 10E to 106 can shift the depth-of-field S to a position away from measurement window 13, to give flexibility to the depth-of-field S to be imaged, without increasing the size of intraoral scanner 100. Therefore, intraoral scanner 100 on which cap 10E to 106 is mounted can obtain data of the three-dimensional shape of a deep portion (root canal portion, for example) of a partially-missing tooth.

Embodiment 4

For Embodiments 1 and 3, it is necessary to mount caps of different types on intraoral scanner 100 in order to shift the depth-of-field of intraoral scar 100. It is therefore necessary for intraoral scanner 100 to determine which type of the cap is mounted on the scanner. For Embodiment 2 as well, it is necessary to determine where the cap is mounted on intraoral scanner 100, because Embodiment 2 can shift the depth-of-field by crag the position where the cap is mounted on intraoral scanner 100. In particular, this determination is important in the situation like Embodiment 3 where the calibration table has to be changed depending on the type of the cap mounted on intraoral scanner 100, and the convenience is improved by automating the determination.

Figure 10A:
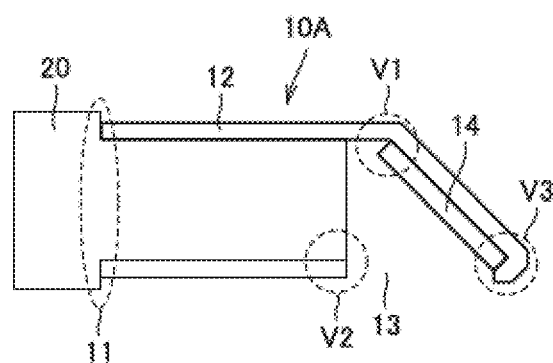
FIG. 10A illustrates an example of determination means for determining the type of the cap according to Embodiment 4.
Figure 10B:
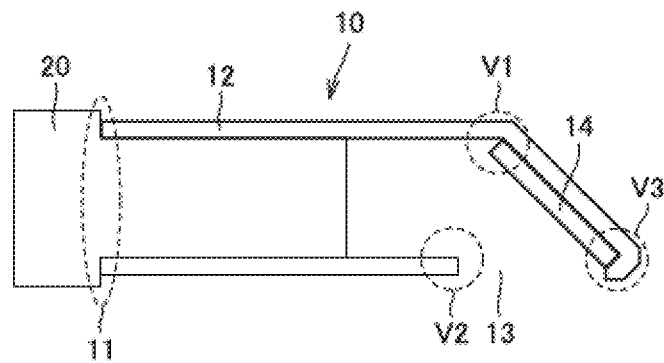
FIG. 10B illustrates an example of the determination means for determining the type of the cap according to Embodiment 4.

FIGS. 10A and 10B illustrate an example of the determination means for determining the type of the cap according to Embodiment 4. Immoral scanner 100 on which a cap is mounted to capture an image of a target can be designed so that a part of the inner wall of the cap and the edges of mirror 14 are to be included in a part of the field of view to be imaged. When cap 10A is mounted on intraoral scanner 100 as shown in FIG. 10A, the field of view to be imaged by intraoral winner 100 includes a part of an inner wall V2 of the cap and a part of edges V1, V3 of mirror 14. Cap 10A has a relatively shorter longitudinal length of housing 12, and therefore, inner wall V2 and edges V1, V3 of mirror 14 that are included in the field of view of immoral scanner 100 appear differently from the case where cap 10 shown in FIG. 10B is mounted.

Controller 40 (or processor 60) can use this difference in appearance of inner wall V2 and edges V1, V3 of mirror 14 to automatically determine whether the cap mounted on immoral scanner 100 is cap 10A which is a cap adapted to the root canal, or cap 10 which is a standard cap.

Controller 40 may also use similar means to automatically determine where the cap is mounted, or whether the cap has an optical element disposed therein. Controller 40 can make the automatic determination for the cap to automatically change the control mode of intraoral scanner 100, depending on the mounted cap. Specifically, controller 40 can change the calibration table, the color of illumination, the light emission intensity, the aperture angle in the case of trigonometry, the zoom lens magnification, and the lens aperture. Moreover, in order to exclude, as invalid data, the image portion located outside the edges of the mirror, the size of the invalid region can be changed depending on the result of determination as to the cap type.

When the cap mounted on intraoral scanner 100 is replaced with a cap of a different type like Embodiments 1 and 3, the type of the cap may be determined based on identification information provided on each cap, rather than based on the determination of the cap type from the difference in appearance of inner wall V2 and edges V1, V3 of mirror 14 of the cap.

Figure 11A:
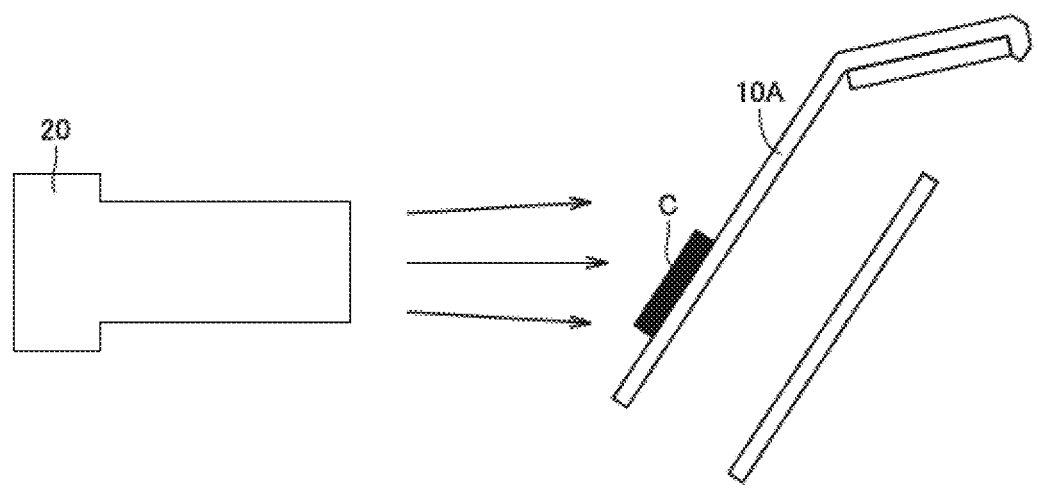
FIG. 11A illustrates another example of the determination means for determining the type of the cap according to Embodiment 4.
Figure 11B:
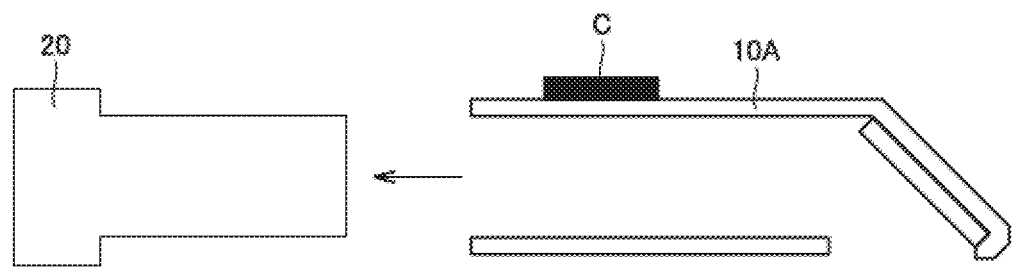
FIG. 11B illustrates a still another example of the determination means for determining the type of the cap according to Embodiment 4.

The identification information to be provided on each cap may be an IC chip containing an RFID (radio frequency identifier), a two-dimensional code or barcode, or the color of the inner wall or the outer wall of the cap, for example. Specifically, the determination means in the case where a code is provided on the outer wall of the cap is described with reference to drawings. FIGS. 11A and 11B illustrate another example of the determination means for the type of the cap according to Embodiment 4.

Referring to FIG. 11A, intraoral scanner 100 captures an image of a two-dimensional code marked an the outer wall of cap 10k Controller 40 (or processor 60) analyzes the image captured by intraoral scanner 100, and controller 40 determines the type of cap 10A with the imaged two-dimensional code. Referring to FIG. 11B, cap 10A of which type has been determined is mounted on intraoral scanner 100. It should be noted that the identification information may be placed inside housing 12 of the cap, and the identification information may be located so that the identification information is included in the captured image when cap 10 has been mounted on tubular portion 20 (being mounted on the tubular portion, for example, partially fit on the tubular portion). In this case, the two steps, namely the first step of orienting the barcode or the like toward the tubular portion and reading the barcode and the second step of mounting the cap on the tubular portion, can be reduced to a single step, which improves the working efficiency of the operator.

Thus, Embodiment 4 includes controller 40 (determiner) capable of determining whether the cap is cap 10 (first cap) defining the depth-of-field of intraoral scanner 100 that extends from measurement window 13 to a predetermined extent or cap 10A (second cap) defining the depth-of-field of intraoral scanner 100 that extends from a position away from measurement window 13 to the predetermined extent, or determining whether cap 10 is mounted at a first position where the depth-of-field of intraoral scanner 100 extends from measurement window 13 to a predetermined extent, or cap 10 is mounted at a second position where the depth-of-field of intraoral scanner 100 extends from a position away from measurement window 13 to the predetermined extent. Further, depending on the result of the determination by controller 40, controller 40 (also functioning as a mode changer) changes the control mode of intraoral scanner 100. It is thus possible to control intraoral scanner 100 in a control mode that is most suitable for the determined type of the cap, according to Embodiment 4.

Embodiment 5

Figure 12A:
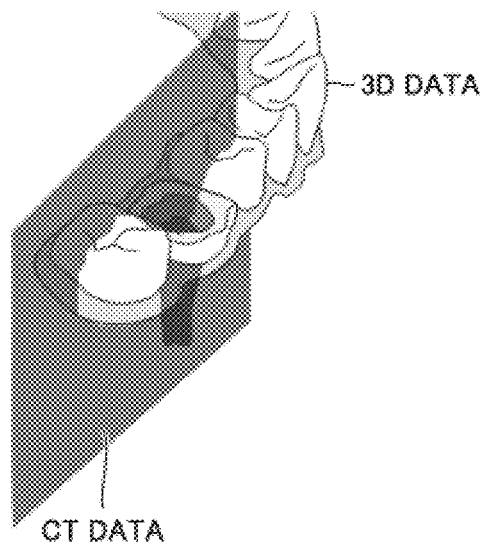
FIG. 12A illustrates an example display of the intraoral scanner according to Embodiment 5.
Figure 12B:
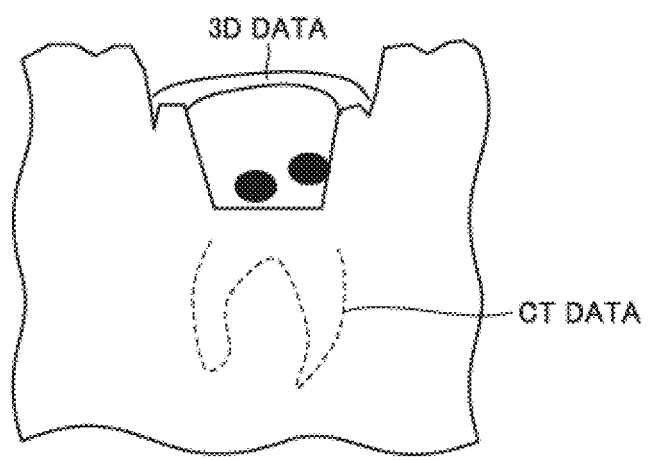
FIG. 12B illustrates an example display of the intraoral scanner according to Embodiment 5.

In connection with Embodiment 1, the example is illustrated where caps of different types are mounted, different data pieces of the three-dimensional shape are obtained by intraoral scanner 100, and these data pieces are combined to be displayed as shown in FIG. 4. In connection with Embodiment 5, an example is illustrated where additional information is further combined for display. FIGS. 12A and 12B illustrate an example display of the intraoral scanner according to Embodiment 5.

FIGS. 12A and 12B show the example where CT data obtained by a CT device is combined with the data of the shape obtained by intraoral scanner 100, and the combined data is displayed.

The data of the shape of the teeth shown in FIG. 4 (*e*) and described in connection with Embodiment 1 is a combination of the data of the three-dimensional shape obtained by intraoral scanner 100 on which the cap for the root canal is mounted, and the data of the shape obtained by intraoral scanner 100 on which die standard cap is mounted. Accordingly, the data of the three-dimensional shape of the teeth includes data of the shallower portion and data of the deeper portion. The user can observe, in an enlarged form, the shape of the entire dental arch and the shape of the root canal of the partially-missing tooth, derived from the data of the three-dimensional shape indicated on display 50.

FIG. 12A shows a state where CT data obtained by a CT device is further combined at the position of the root canal of the partially-missing tooth and displayed (here, by way of example, a specific cross section derived from the CT data is laid to overlap the three-dimensional data (3D data) of the teeth and displayed). Therefore, the data of the shape of the tooth with which the CT data is combined includes data of a portion (an in vivo image, such as an image of a root apex, for example) that is not seen through intraoral scanner 100. The user can not only observe, in an enlarged fob the shape of the whole dental arch and the shape of the root canal of the partially-missing tooth derived from the data of the three-dimensional shape shown on display 50, but also identify them as a whole that further includes the root apex in the living organism. The CT data in the form of data of a two-dimensional cross section may be laid to overlap the three-dimensional data and displayed as shown in FIGS. 12A and 12B, or the CT data may be subjected to surface rendering and the resultant CT data may be laid to overlap the data and displayed three-dimensionally. Such different types of data can be laid to overlap by making coordinate adjustments using a known method such as ICP (Iterative Closest Point) algorithm applied to the data obtained through scanning by the intraoral scanner and the surface data obtained through the aforementioned surface rendering.

Thus, according to Embodiment 5, when intraoral scanner 100 acquires a CT image of a tooth where the portion extending from the occlusal portion toward the alveolar bone is missing, the three-dimensional data of teeth including the occlusal portion, data of a tooth where the occlusal portion is missing and the portion extending from the occlusal portion toward the alveolar bone remains, and the CT image are laid on each other and indicated on display 50. Thus, according to Embodiment 5, the information that cannot be obtained through intraoral scanner 100 can be provided, in combination with the data of the shape, to the user.

The information that can be combined with the data of the shape of teeth is not limited to the CT data obtained by means of a CT device, but may be in-vivo information (information about the inside of a living organism) obtained by means of any of other devices, such as tomographic data obtained by means of an OCT device, a X-ray image obtained by means of an X-ray imaging device, an ultrasonic diagnosis image, and an infrared image.

Modifications

While the caps and the image capturing device according to Embodiments 1 to are described herein as being used for an intraoral scanner, the use is not limited to the intraoral scanner. For example, the caps and the image capturing device according to Embodiments 1 to 5 may be used for an image capturing device such as intraoral camera, optical coherence tomography (OCT) device, ultraviolet/infrared/terahertz imaging device, fluorescent imaging device, and the like, for example.

While the image capturing device according to Embodiments 1 to 5 is described herein as being applied to human root canal treatment by way of example, the image capturing device is also applicable to other conditions. The image capturing device is applicable usefully as well to evaluation of an implant abutment located further away from the crown, for example, and dental diagnosis for animals having longer teeth than human teeth. Moreover, the image capturing device may be applied not only to teeth and gums in the oral cavity but also to other living organism tissues such as external auditory meatus, and may also be applied to a gap between walls of buildings, the inside of a pipe, or an industrial product having a hollow cavity. The present disclosure is thus applicable widely to uses for measuring/observing the inside of a space that is narrow and likely to have blind spots.

It should be construed that the embodiments of the present disclosure described herein are given by way of illustration in all respects, not by way of limitation. It is intended that the scope of the present disclosure is defined by claims, and encompasses all modifications and variations equivalent in meaning and scope to the claims.

What is claimed is:

1. A cap mountable on and detachable from an image capturing device constituting an intraoral scanner that obtains, as three-dimensional data, a shape of a tooth in an oral cavity, the cap comprising:
    a housing having an opening that permits connection to at least a part of the image capturing device;
    a light inlet disposed in the housing and located opposite to the opening; and
    a reflector that reflects light from the light inlet toward the opening, wherein
    the housing, when connecting to the part of the image capturing device, has a longitudinal length shorter than a longitudinal length of a housing of a specific cap that is mounted on the image capturing device and that can obtain three-dimensional data of a tooth including an occlusal portion, and
    the longitudinal length of the housing of the cap is the length at which the image capturing device can obtain three-dimensional data of a tooth where the occlusal portion is missing and a portion extending from the occlusal portion toward an alveolar bone remains.

2. The cap according to claim 1, wherein the image capturing device is an intraoral scanner that obtains, as three-dimensional data, a shape of a tooth in an oral cavity.

3. An image capturing device comprising:
    the cap according to claim 1; and
    a tubular portion connected detachably to the cap.

4. The image capturing device according to claim 3, further comprising:
    determination circuitry configured to make a determination as to
        whether the cap is a first cap defining a depth-of-field of the image capturing device that extends from the light inlet to the predetermined extent, or a second cap defining a depth-of-field of the image capturing device that extends from a position away from the light inlet to the predetermined extent, or
        whether the cap is mounted at a first position defining a depth-of-field of the image capturing device that extends from the light inlet to the predetermined extent, or the cap is mounted at a second position defining a depth-of-field of the image capturing device that extends from a position away from the light inlet to the predetermined extent; and
    mode changing circuitry configured to change a control mode of the image capturing device in accordance with a result of the determination made by the determination circuitry.

5. The image capturing device according to claim 4, wherein
    the image capturing device is an intraoral scanner that obtains, as three-dimensional data, a shape of a tooth in an oral cavity,
    when the first cap is mounted on the image capturing device or the cap is mounted at the first position, the image capturing device obtains three-dimensional data of a tooth including an occlusal portion, and
    when the second cap is mounted on the image capturing device or the cap is mounted at the second position, the image capturing device obtains three-dimensional data of a tooth where the occlusal portion is missing and a portion extending from the occlusal portion toward an alveolar bone remains.

6. The image capturing device according to claim 5, wherein
    when the image capturing device obtains in-vivo information about an inside of a living organism that includes a tooth, where the portion extending from the occlusal portion toward the alveolar bone is missing, the image capturing device causes a display to show the three-dimensional data of the tooth including the occlusal portion, the three-dimensional data of the tooth where the occlusal portion is missing and the portion extending from the occlusal portion toward the alveolar bone remains, and the in-vivo information in an overlapping manner.

* * * * *